United States Patent [19]

Dubrul et al.

[11] Patent Number: 5,183,464
[45] Date of Patent: Feb. 2, 1993

[54] RADIALLY EXPANDABLE DILATOR

[75] Inventors: William R. Dubrul, Redwood City; Cecily M. Hillsman, San Jose, both of Calif.

[73] Assignee: Interventional Thermodynamics, Inc., Mountain View, Calif.

[21] Appl. No.: 702,642

[22] Filed: May 17, 1991

[51] Int. Cl.$^5$ .................... A61M 29/00; A61B 1/32
[52] U.S. Cl. ........................... 128/3; 606/108; 604/96; 604/164; 604/104
[58] Field of Search .................... 604/51-54, 604/93, 96, 104, 158, 160, 164, 171, 172, 174, 175, 264, 280, 282; 606/191, 198; 623/12; 128/3

[56] References Cited

U.S. PATENT DOCUMENTS

| | | | |
|---|---|---|---|
| 668,879 | 2/1901 | Miller | 606/198 X |
| 1,213,001 | 1/1917 | Philips . | |
| 1,248,492 | 12/1917 | Hill . | |
| 2,548,602 | 4/1951 | Greenburg . | |
| 3,545,443 | 12/1970 | Ansari . | |
| 3,631,852 | 1/1972 | Hay et al. | 128/3 |
| 3,742,958 | 7/1973 | Rundles . | |
| 3,789,852 | 2/1974 | Kim et al. | 606/198 X |
| 3,902,492 | 9/1975 | Greenhalgh . | |
| 4,141,364 | 2/1979 | Schultze . | |
| 4,411,655 | 10/1983 | Schreck | 604/165 |
| 4,479,497 | 10/1984 | Fogarty et al. . | |
| 4,581,025 | 4/1986 | Timmermans . | |
| 4,589,868 | 5/1986 | Dretler . | |
| 4,601,713 | 7/1986 | Fuqua . | |
| 4,716,901 | 1/1988 | Jackson et al. | 606/198 X |
| 4,738,666 | 4/1988 | Fuqua . | |
| 4,739,762 | 4/1988 | Palmaz | 604/104 X |
| 4,772,266 | 9/1988 | Groshong . | |
| 4,798,193 | 1/1989 | Giesy et al. | 128/7 |
| 4,846,791 | 7/1989 | Hattler et al. | 604/43 |
| 4,865,593 | 9/1989 | Ogawa et al. . | |
| 4,888,000 | 12/1989 | McQuilkin et al. . | |
| 4,896,669 | 1/1990 | Bhate et al. . | |
| 4,899,729 | 2/1990 | Gill et al. | 128/3 |
| 4,921,479 | 5/1990 | Greyzel | 604/53 |
| 4,955,895 | 9/1990 | Sugiyama et al. . | |
| 4,972,827 | 11/1990 | Kishi et al. | 128/3 |
| 4,986,830 | 1/1991 | Owens et al. . | |
| 5,116,318 | 5/1992 | Hillstead | 604/96 |
| 5,139,511 | 8/1992 | Gill et al. | 606/198 |

Primary Examiner—John D. Yasko
Assistant Examiner—Adam J. Cermak
Attorney, Agent, or Firm—Townsend and Townsend

[57] ABSTRACT

An apparatus for forming and enlarging percutaneous penetrations comprises an elongate dilation tube which receives an elongate expansion member in an axial lumen thereof. The dilation tube is radially expandable from a small diameter configuration to a larger diameter configuration. The dilation tube is percutaneously introduced to a desired target site within a patient's body and thereafter radially expanded by axial insertion of the expansion member through the axial lumen of the tube. The tube prevents the application of axial forces on the surrounding tissue as the expansion member is introduced. The expansion member may include a separate outer sleeve member which remains in place to maintain the enlarged access channel. Optionally, an inflatable balloon at the distal end of the dilation tube may be provided to enhance retention of the device and sealing of the penetration.

58 Claims, 5 Drawing Sheets

RADIALLY EXPANDABLE DILATOR

BACKGROUND OF THE INVENTION

1. Field of the Invention

The present invention relates generally apparatus and method for providing percutaneous access to hollow body organs, tissue, and cavities. More particularly, the present invention relates to the construction and use of a dilator device which facilitates radial expansion of small diameter access punctures to create larger diameter working channels for subsequent introduction of instruments, medication, fluids, and the like.

Modern medicine frequently requires percutaneous access to hollow body organs, tissue, cavities, and the like. In the case of "least or minimally invasive" surgical procedures, such access is usually provided by inserting a suitable cannula, instrument, tube, or the like, through a small access hole. The initial access is usually created by piercing the skin and any intermediate body structures with a needle or trocar. The initial puncture, however, is usually very small so that the needle or trocar can achieve the desired penetration without excessive damage to tissue. It is therefore necessary for the initial access hole to be subsequently enlarged to provide a working channel having a sufficient diameter to permit performance of the desired medical procedure.

One common technique for achieving such enlargement relies on successively introducing one or more dilating rods having increasingly larger diameters through the puncture hole and into the body organ, tissue, or cavity. When a flexible guide wire has been introduced through the initial needle or cannula puncture, this protocol is referred to as the Seldinger technique.

While this technique is reasonably effective for placement of relatively small devices, e.g., catheters to about 6 French (F; 0.079 inch diameter), larger dilations require increasing numbers of dilator exchanges and can be extremely time consuming. Moreover, the body structures that are being penetrated frequently comprise relatively flaccid membranes or walls so that penetration with larger dilators may cause fascial detachment, i.e., the invagination and separation of the membrane or wall from surrounding tissue structures. Such problems may be exacerbated when the organ, tissue, or cavity being penetrated is diseased so that the membranes or walls are thickened or toughened and resistant to penetration by the dilator which axially engages the tissue.

One approach for preventing fascial detachment of the internal body organ or structure during the dilation process involves the use of separate anchoring instruments which are placed around the site of penetration and dilation. The technique, developed by Dr. Cope, relies on the placement of multiple separate anchors or toggles peripherally about the site of the primary puncture in order to more strongly attach the body organ to its surrounding fascia. The anchors are attached to lengths of suture which extend through the tracks defined by the separate punctures. The sutures are tensioned in order to hold the wall of the hollow organ against the fascia and subsequently secured outside the body. While this approach is generally successful, it requires a separate puncture for each anchor and the subsequent suturing of each anchor in place. The technique is therefore relatively time consuming, costly, and potentially subjects the patient to greater discomfort.

An additional problem with the use of successively larger dilators, either with or without use of the Cope anchoring technique, is the leakage of body fluids and substances through the penetration which is being enlarged While such leakage will be inhibited while each successive dilator is in place, removal of the dilator will allow the fluids from the organ, tissue or cavity being penetrated to contaminate other body structures on the puncture track. For example, percutaneous access to the gallbladder is normally achieved transhepatically since the gallbladder is partially attached to the liver. Transperitoneal access proceeds through an unattached wall of the gallbladder and increases the likelihood of bile leakage into the peritoneal. While transperitoneal access might otherwise be preferred for a number of reasons, e.g., it avoids potential damage to the liver, it is contraindicated by the difficulty in penetrating the unattached wall of the gallbladder and the greater risk of bile leakage associated with conventional dilation techniques.

For these reasons, it would be desirable to provide improved methods and apparatus for forming and enlarging percutaneous penetrations into hollow body organs, tissues, and cavities. The apparatus and methods should be suitable for enlarging percutaneous access penetrations to virtually any diameter, including very large diameters on the order of 20 F, 24 F, and larger while reducing the risk of invagination and fascial detachment of the organ, tissue, or cavity which is being penetrated. The methods should minimize any additional time and complexity required for performing an associated interventional procedure, and in particular, should avoid the need to make secondary penetrations in order to secure the body organ, tissue, or cavity to surrounding fascia. The methods should further avoid complexity and will preferably reduce the number of incremental dilations required to achieve a desired enlargement. The method should also lessen the patient discomfort associated with the procedure and should be compatible with virtually any type of interventional procedure which requires the formation of a percutaneous penetration for access to the body organ, tissue, or cavity.

2. Description of the Background Art

U.S. Pat. No. 4,738,666, describes an expandable catheter having an external sheath which is perforated to facilitate removal as the catheter is being expanded. U.S. Pat. No. 4,601,713, describes a variable diameter catheter having an inflatable retention balloon at its distal end. The catheter is introduced with an internal stylet which holds the catheter in a collapsed (reduced diameter) configuration. Removal of the stylet allows the catheter to expand. U.S. Pat. No. 4,141,364, describes an expandable endotracheal tube which is inserted in a collapsed configuration and springs back to an expanded configuration when air is introduced. Inflatable dilator apparatus are described in U.S. Pat. Nos. 4,589,868 and 2,548,602. Catheters having expandable structures are described in U.S. Pat. Nos. 4,986,830; 4,955,895; 4,896,669; 4,479,497; and 3,902,492.

U.S. Pat. No. 4,772,266, describes a dilator/sheath assembly that may be passed over an indwelling guide wire in order to enlarge an access hole, with entry of the sheath further enlarging the hole. U.S. Pat. No. 1,213,001, describes a trocar and cannula assembly which includes an intermediate tube to form a three-piece structure. U.S. Pat. No. 3,742,958, discloses a cannula having an axial slot to allow the cannula to be stripped from a working catheter which has been introduced through the cannula. U.S. Pat. Nos. 4,888,000; 4,865,593; 4,581,025; 3,545,443; and 1,248,492, each describe devices suitable for percutaneous penetration of a body cavity, blood vessel, or solid tissue. The disclosures of each of the U.S. Patents cited in this paragraph are hereby incorporated herein by reference.

Methods which rely on the percutaneous introduction of a catheter into the gallbladder and other hollow body organs are described in copending application Ser. Nos. 07/407,839; 07/529,077; and 07/551,971, the disclosures of which are incorporated herein by reference. A dilator assembly including a guide member having an anchor at its distal end is described in copending application Ser. No. 07/616,122, the disclosure of which is incorporated herein by reference.

SUMMARY OF THE INVENTION

According to the present invention, improved apparatus and methods for forming and enlarging percutaneous penetrations into target locations within a patient's body are provided. The apparatus comprises an elongate dilation tube having a proximal end, a distal end, and an axial lumen extending between said ends. The elongate dilation tube is radially expandable from a small diameter to a large diameter, where the small diameter is sufficiently small to permit substantially unimpeded penetration through tissue and other body structures and the larger diameter is sufficiently large so that its expanded axial lumen provides an access channel capable of receiving a wide variety of surgical devices, working catheters, tubes, and the like.

The elongate dilation tube may comprise a single folded or elastic tube having a lubricous coating on its inner lumen. Alternatively, the elongate dilation tube can have a layered or laminate structure including an outer elastic sheath and a separate lubricous inner sleeve. In the latter case, the lubricous inner sleeve will frequently be folded or have an overlapped structure to facilitate expansion as described hereinbelow. Numerous other specific constructions will also be possible so long as the tube can assume an initial collapsed configuration having a sufficiently narrow outer diameter to facilitate penetration and a subsequent expanded configuration after passage of an elongate expansion member therethrough (as described hereinafter).

The apparatus of the present invention optionally includes means at the distal end of the elongate dilation tube for puncturing skin and underlying tissue and organs as the dilation tube is percutaneously advanced toward the desired target location. Conveniently, the puncturing means may comprise a sharpened tip formed either integrally or separately on the distal end of the dilation tube. Alternatively, the sharpened tip may be provided by a separate stylet which is disposed within the axial lumen of the elongate dilation tube while the tube is being advanced toward the target location. In the latter case, the stylet will be removed prior to radial expansion of the dilation tube. The second alternative for providing the sharpened tip is a separate needle which receives the elongate dilation member in the needle lumen. The needle is introduced to the desired target location by conventional puncture techniques and then withdrawn to leave the elongate dilation tube in place.

The apparatus of the present invention, however, need not comprise a sharpened distal tip. The device may be inserted through a small puncture which has been formed and partially dilated using conventional apparatus and techniques. Such initial dilation will usually be used to enlarge the puncture until it is sufficiently large to accept the apparatus of the present invention but which is still substantially smaller than the desired final diameter. Typically, such a dilated intermediate puncture will have a diameter in the range from about 3 to 8 French, usually being in the range from about 5 to 7 French. The apparatus of the present invention may have a tapered (but not sharpened) distal end when used with such "pre-enlargement."

The apparatus of the present invention further includes an elongate expansion member which is insertable through the axial lumen of the elongate dilation tube to effect radial expansion thereof. The elongate expansion member can be a single rod which is inserted fully into the elongate tube to achieve expansion along its entire length and then immediately removed. In such a case, the elongate dilation tube must be sufficiently rigid so that it can retain its expanded shape without additional support. More commonly, in the case of less rigid and elastic elongate dilation tubes, the elongate expansion member will comprise an assembly of a rigid or semi-rigid outer tube and inner rod where the entire assembly is inserted to effect radial expansion of the elongate dilation tube. The inner rod is then removed, leaving the outer tube in place to maintain a desired expanded access channel to the target location.

Optionally, the apparatus of the present invention may further comprise an inflatable balloon or other expandable sealing and retention member at the distal end of the elongate tube. A means is provided for inflating the balloon from the proximal end to effect sealing of the percutaneous penetration which is formed. The balloon also permits the user to apply axial tension in the proximal direction on the apparatus in order to compress the tissue surrounding penetration and further inhibit facial detachment as the expansion member is inserted. Usually, the inflating means will be a lumen formed in the elongate dilation tube itself, typically in the outer elastic sheath when the elongate member comprises a laminated structure.

The method of the present invention comprises percutaneously penetrating the elongate dilation tube, so that its distal end lies within the desired target location within the patient's body. The target may be a hollow body organ, solid tissue location, body cavity, or the like. After penetration, the elongate dilation tube is radially expanded by inserting the elongate expansion member through the axial lumen of the tube. The resulting expanded axial lumen of the tube defines the desired enlarged percutaneous access channel to the target location. When the elongate dilation tube includes a separate stylet (to facilitate initial placement), the stylet will be removed prior to radial expansion with the elongate expansion member. When the elongate dilation tube comprises an outer tube and inner rod, the outer tube will usually be left within the dilation tube after expansion to maintain the enlarged access channel. Optionally, a balloon at the distal end of the elongate dilation tube may be inflated to enhance sealing of the tube to the surrounding percutaneous penetration and retention of the assembly within the target location.

BRIEF DESCRIPTION OF THE DRAWINGS

The illustrations in the drawings are generally not to scale. Reference should be made to the dimensions provided in the specification rather than to the relative

DESCRIPTION OF THE SPECIFIC EMBODIMENTS

Figure 1:
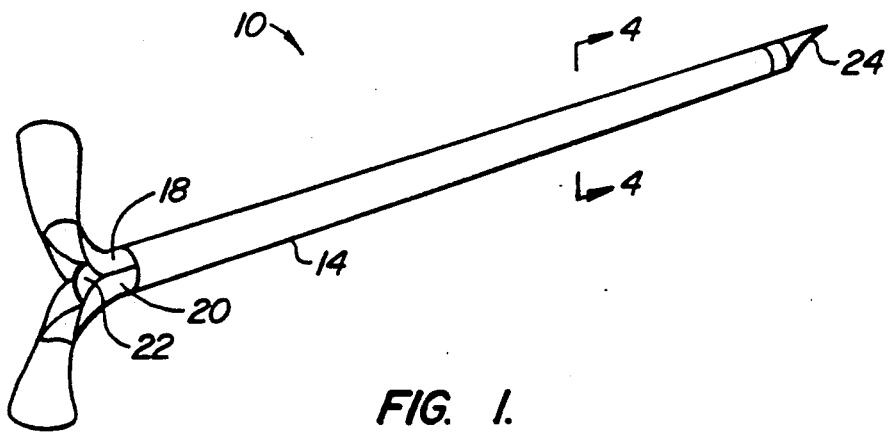
FIG. 1 is a perspective view of an elongate dilation tube constructed in accordance with the principles of the present invention.

The present invention is useful for forming and enlarging percutaneous penetrations to a variety of target locations within a patient's body for a multiplicity of purposes. The initial penetration will be very small, usually being below about 7 F, more usually being below about 3 F, and frequently being below about 20 GA (gauge; 0.35 in). The penetration will subsequently be enlarged to a desired final size, usually having a final diameter in the range from about 10 French (F) to about 30 F, typically being from about 12 F to 28 F, and usually being from about 14 F to 24 F, with the present invention being particularly useful for the formation of larger diameter penetrations.

The purpose of the penetration can be for drainage, intraorgan drug administration, feeding, perfusion, aspiration, or the like, but will usually be for the introduction of a relatively large surgical instrument or working catheter, such as those intended for least invasive surgical procedures. Such procedures include laparoscopy, balloon dilation of ducts, placement of stents, urological and biliary stone removal, and the like. The enlarged penetrations formed by the apparatus and methods of the present invention are particularly suitable for the introduction of thermal ablation catheters, such as those described in copending applications serial nos. 07/407,829; 07/529,077; 07/551,971; 07/702,796, the disclosures of which are incorporated herein by reference, to the gallbladder.

The target locations for the percutaneous penetrations will usually be the interior of a hollow body organ or body cavity, such as the gallbladder, stomach, urinary bladder, uterus, kidney, portions of the lung, rectum, the peritoneum, and the like. The target locations may also be situated within solid tissue as well as solid organs, such as a solid tumor or abscess. Depending on the location which is being accessed, the length and flexibility of the apparatus of the present invention may vary significantly. Dilation apparatus according to the present invention includes an elongate dilation tube having an axial lumen which defines a path for the introduction of one or more elongate expansion members. The elongate dilation tube will have proximal and distal ends, and may have generally flexible or rigid structure, depending on the particular application. Rigid or semi-rigid dilation tubes will generally be employed when the target organ may be approached along a substantially straight path, while more flexible dilation tubes will be employed when the access route is more tortuous.

The length of the elongate dilation tube will vary, with shorter dilation tubes typically having a length in the range from about 7 cm to 12 cm and being suitable for accessing target locations which are near the surface of the skin, such as the stomach. Longer dilation tubes will have a length in the range from about 15 cm to 25 cm and will be suitable for accessing more remote target locations, such as the kidney. Even longer flexible dilation tubes having lengths in the range from about 30 cm to 50 cm, or longer, may be employed for accessing the most remote ducts and body locations.

The elongate dilation tube will be formed to be radially expandable, i.e., expandable from a very small initial outside diameter, typically at or below the diameters described above, to a much larger diameter which will afford an access channel having a diameter within the ranges set forth above. The specific nature and structure of the elongate tube is not critical so long as it is able to receive the expansion member in its axial lumen and permit the expansion member to be advanced axially forward to cause radial expansion of the tube. Thus, the elongate dilation tube will be deformable, elastic, or otherwise expandable in the radial direction to permit the desired radial dilation as the expansion member is axially advanced. The dilation tube will usually have a lubricous inner surface on the axial lumen to facilitate such axial advancement of the expansion member, although in some cases it may be sufficient to provide a lubricous outer surface on the expansion member itself.

Radially expandable dilation tubes which are elastic will typically be formed at least in part from natural or synthetic elastomers, such as latex or silicone rubber. In such cases it will usually be required to provide a lubricous inner coating or sleeve in order to facilitate axial advancement of the expansion member, as described in more detail hereinbelow. Moreover, it will usually be necessary to provide separate means for maintaining the expanded radius of the access channel formed after insertion of the dilation member, i.e., to prevent the elastic wall from collapsing. Conveniently, this may be achieved by including a separate outer tube on the expansion member, where the tube is left in place to maintain the access channel, as described in more detail hereinbelow.

Alternatively, the elongate dilation tube can be formed from a deformable material, such as a metal or organic polymer, e.g. polyethylene, which can be expanded by the expansion member one time and which will thereafter retain its expanded diameter. Metallic deformable dilation tubes will usually be folded, layered, nested, or otherwise configured to have a reduced initial diameter to permit percutaneous penetration. After penetration, upon insertion of the expansion member, the dilation tube will unfold or otherwise open to its final desired diameter and will be sufficiently rigid to maintain the expanded diameter for an indefinite period. In this way, the dilation tube itself can provide the access channel in its enlarged axial lumen.

When the elongate dilation tube is formed from a deformable organic polymer, such as flexible polyethylene, a significant portion of the dilation is permanent. Plastic flow will increase the inside and outside diameters while thinning the wall section. In this alternate construction, an interior rigid or semi-rigid sleeve (as described in more detail hereinafter) will be necessary to maintain the enlarged axial lumen.

Frequently, the elongate dilation tube will have a laminate or layered structure including two or more coaxial components. In this way, various desired structural properties can be combined in the dilation tube. In an exemplary embodiment described in detail hereinbelow, the dilation tube includes an outer elastic sheath and an inner lubricous sleeve, where the elastic sheath provides for controlled radial expansion while the lubricous sleeve facilitates introduction of the expansion member and provides for axial rigidity. The lubricous sleeve is conveniently formed from a highly lubricous plastic, such as Teflon ®, and the like.

Means will be optionally provided at the distal end of the elongate dilation tube for puncturing the skin and underlying tissue, organs, and the like, as the tube is percutaneously advanced toward its target location. Conveniently, when the elongate tube possesses a sufficient degree of axial rigidity or stiffness, a sharpened tip may be provided at the distal end of the tube itself. In an exemplary embodiment described hereinafter, the sharpened tip is an integral portion of the lubricous inner sleeve, although this would not necessarily be the case in all embodiments, i.e., the tip could be separately attached to either the tube itself or the sleeve, or could be formed integrally as part of the tube. In the case of dilation tubes which are less rigid, it will usually be necessary to provide a separate, relatively stiff stylet or needle to facilitate percutaneous penetration. Conveniently, a stylet having a sharpened distal tip may be placed in the axial lumen of the dilation tube so that the sharpened tip is exposed at the distal end of the combined assembly. The assembly can then be percutaneously advanced to the target location and the stylet removed prior to radial expansion of the tube, as described hereinafter. Alternatively, for elongate dilation tubes having very small initial diameters, it will be possible to insert the tube in the lumen of a separate needle. The needle can be introduced to the desired target location, and the needle can then be withdrawn, leaving the dilation tube in place.

A sharpened tip or other means for puncturing the skin will be necessary when no previous needle puncture will have been made. The present invention, however, is useful in cases where conventional techniques and apparatus are used to form an initial, relatively small diameter, puncture. Typically, the puncture will be made using a very small needle, and it will be possible in some cases to introduce the dilation tube of the present invention (without a sharpened tip) directly into the initial puncture track. More commonly, the initial puncture track will be subsequently enlarged to an intermediate diameter using conventional techniques and apparatus, such as the Seldinger technique combined with very small axial dilation. The dilated intermediate diameter will typically be in the range from about 3 F to 8 F, more typically being in the range from about 5 F to 7 F. The dilation tube of the present invention may then be introduced into the partially dilated penetration, typically over a flexible guide wire or other member which has been left in place to maintain the track. The penetration may then be enlarged by the subsequent axial introduction of the expansion member or members in order to achieve the final desired diameter for the access lumen.

The elongate expansion member will have a length which is generally equal to that of the dilation tube, usually being slightly longer to facilitate manipulation, and will have an outer diameter which is larger than the diameter of the axial lumen of the dilation tube. Usually, the diameter of the dilation member will be sufficient to radially expand the dilation tube to its final desired diameter, although in some cases it may be desirable to employ two or more dilation members having successively larger diameters to provide for an incremental expansion. Typically, the outer diameter of the expansion member will be at least two fold larger than the diameter of the dilation tube lumen, usually being at least three fold larger, and frequently being five fold or more larger.

The elongate expansion member will usually have a slightly tapered distal end to facilitate introduction through the axial lumen of the dilation tube. Additionally, the exterior surface of the expansion member may be wholly or partly coated with a lubricant to further facilitate penetration, although this may not be necessary when the inner surface of the axial lumen of the tube is itself lubricous.

Most simply, the elongate expansion may be a single rod or shaft which can be advanced through the axial lumen of the dilation tube to effect radial expansion as it proceeds toward the target location. After the dilation tube is fully expanded, the rod or shaft can then be removed, leaving the expanded axial lumen of the dilation tube. This approach, however, will only be effective when the dilation tube is sufficiently rigid to maintain the expanded radial diameter by itself.

For less rigid dilation tubes, i.e., those which are not able to maintain an expanded radial configuration, it will be necessary to provide a separate component to hold the expanded access channel open. Conveniently, this can be provided as part of the expansion member itself, typically by including both an outer tube and an inner rod member. The assembly of the outer tube and the inner rod is inserted as the dilation member into the axial lumen of the dilation tube. The outer tube will be non-collapsible under the range of compressive or elastic return forces created by expansion. The outer tube will typically be formed from a semi-rigid or rigid plastic or from metal, and will be able to maintain the desired access channel after the inner rod is removed. The outer tube, of course, need not be a continuous cylinder and instead could be a mesh, perforate cylinder, or any other structure which, when left in place, will maintain the expanded lumen of the dilation tube.

Optionally, an inflatable balloon will be disposed at or near the distal end of the elongate dilation tube.

Means for inflating the balloon, typically a lumen formed in the tube and extending to the proximal end, will also be provided. The balloon will usually be formed from conventional elastic balloon materials, such as silicone and latex rubbers, and the like. The purpose of the balloon is two-fold. First, when the tube is placed under tension, the inflated balloon will draw the intermediate tissue structures together. Second, the balloon will enhance sealing of the dilation tube to the tissue or body structure which is being dilated. The balloon, however, is not always necessary since the radial expansion of the dilation tube itself will often prevent tissue delamination and provide a highly effective seal preventing loss or contamination of body fluids.

The dimensions of the balloon are not critical and will be selected to provide a balloon diameter when inflated which is sufficient to effect the desired sealing and retention of the dilation tube. The diameter of the balloon will usually be at least 20% greater than that of the dilation tube after radial expansion, usually being at least about 10% greater. Thus, the balloon will typically have a diameter when inflated in the range from about 1 mm to 10 mm, more usually being in the range from about 2 mm to 6 mm.

Figure 2:
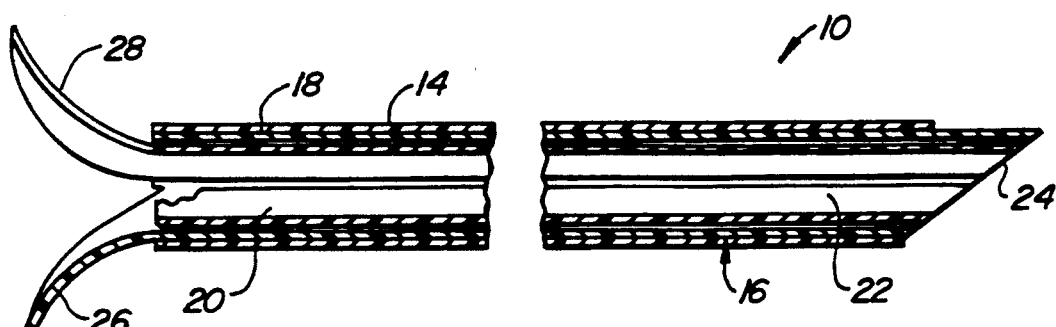
FIG. 2 is a side elevational view of the elongate dilation tube of FIG. 1.
Figure 3:
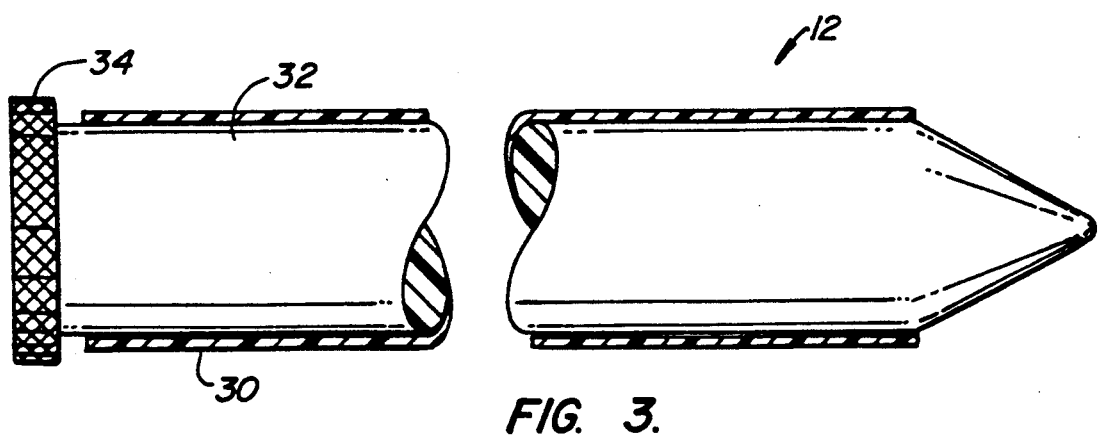
FIG. 3 is an elongate expansion member constructed in accordance with the principles of the present invention and useful in combination with the elongate dilation tube of FIGS. 1 and 2.
Figure 4:
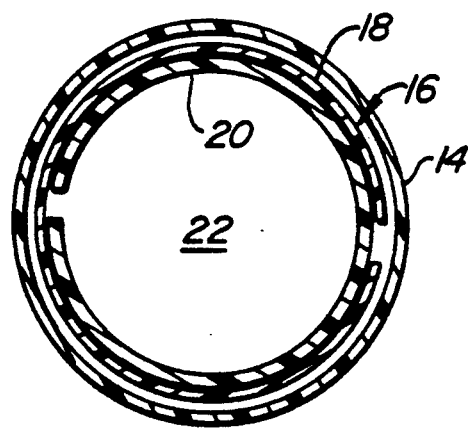
FIG. 4 is a cross-sectional view taken along line 4—4 of FIG. 1.

Referring now to FIGS. 1-6, a first exemplary embodiment of a percutaneous penetration apparatus constructed in accordance with the principles of the present invention will be described. The apparatus includes an elongate dilation tube 10 (FIGS. 1 and 2) and an elongate expansion member 12 (FIG. 3). The dilation tube 10 comprises an outer elastic sheath 14 and an inner lubricous sleeve 16, with sleeve 16 consisting of a pair of nested cylinders 18 and 20, as best observed in FIG. 4. The sheath 14 is formed from a natural or synthetic rubber, typically silicone rubber or a deformable plastic material, and acts as a band holding the cylinders 18 and 20 of the lubricous sleeve together. In its initial configuration, as illustrated in FIGS. 1, 2, the dilation tube has an axial lumen 22 with a relatively small diameter.

In this embodiment, the dilation tube 10 includes a sharpened tip 24 at its distal end. Conveniently, the sharpened tip 24 is formed by tapering the distal end of the lubricous sleeve 16. Dilation tube 10 further includes a pair of tabs 26 and 28 at its proximal end. The tabs 26 and 28, which are formed as proximal extensions of the lubricous tube 16, permits the user to secure the dilation tube 10, typically by holding the tabs manually, as the dilation member is inserted. The expansion member 12 includes an outer tube 30 and an inner rod 32. The inner rod includes a knob 34 at its proximal end to facilitate manipulation.

Figure 5:
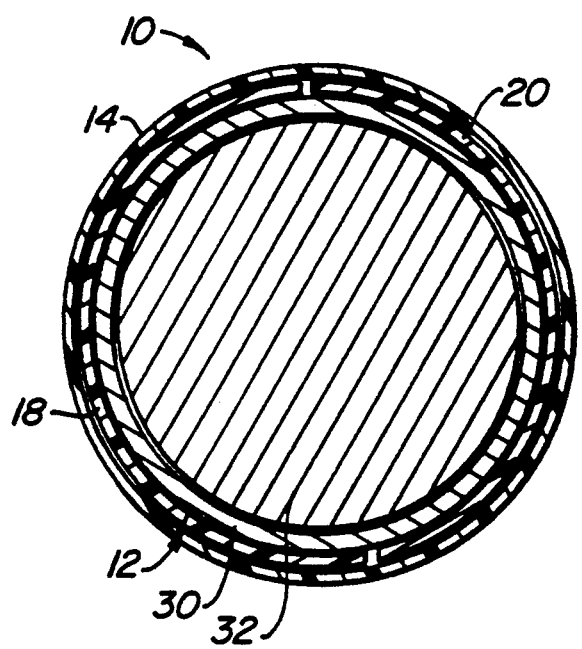
FIG. 5 is a cross-sectional view similar to that of FIG. 4, except that the elongate dilation tube has been radially enlarged by insertion of the elongate expansion member of FIG. 3.
Figure 6:
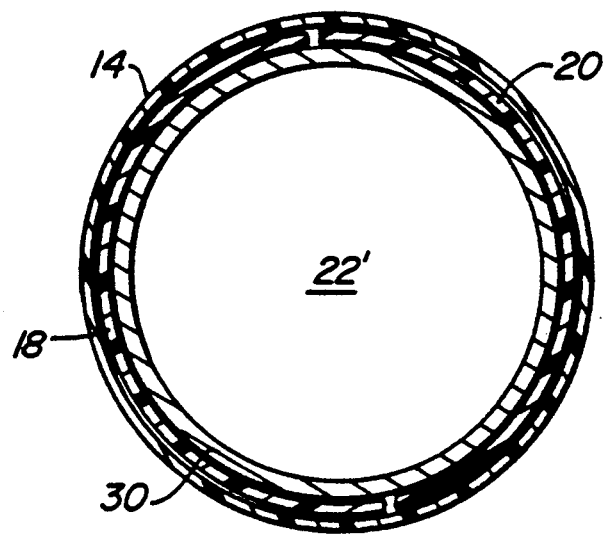
FIG. 6 is a cross-sectional view similar to that of FIG. 5, except that an inner rod of the elongate expansion member has been removed, leaving an enlarged access channel.

The dilation member 12 may be inserted into the axial lumen 22 of the dilation tube 10, resulting in expansion of the dilation tube, as best observed in FIG. 5. After the dilation tube 10 has been expanded, the inner rod 32 may be removed, leaving an expanded access channel 22' (FIG. 6) which is maintained by the outer tube 30.

An alternate exemplary embodiment of the percutaneous penetration apparatus of the present invention is illustrated in FIGS. 7-10. The alternate embodiment differs from the previous embodiment in the inclusion of an inflatable sealing balloon at the distal end of the elongate dilation tube, the use of a separate stylet for facilitating initial introduction of the dilation tube, and a unitary (non-laminated) structure for the dilation tube.

The dilation tube 40 is formed from an elastic material, such as latex or silicone rubber or a permanently deformable plastic such as polyethylene. A tube 40 is typically formed by extrusion and will include a first lumen 42 (FIG. 8) and a balloon inflation lumen 44. The balloon inflation lumen 44 opens into a balloon structure 46 through a port 48. At its proximal end, inflation lumen 44 terminates in a side connector or port 50.

Figure 7:
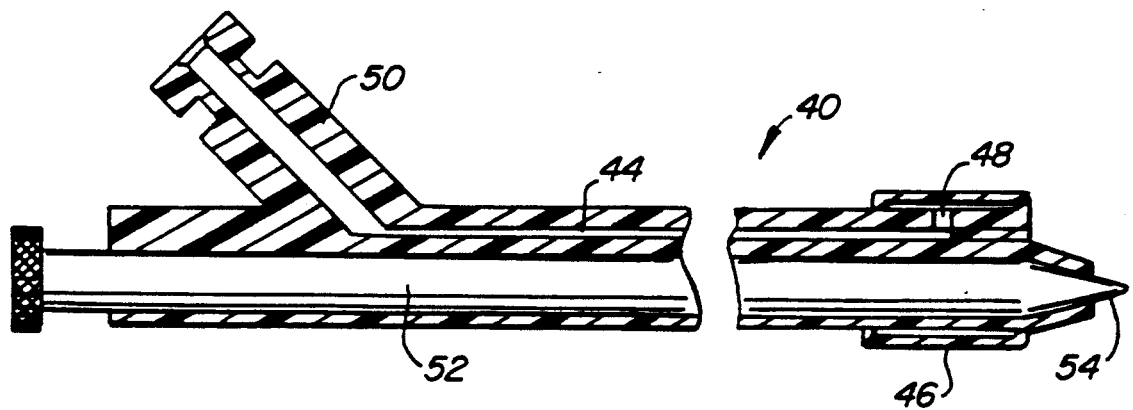
FIG. 7 illustrates an alternate embodiment of an elongate dilation tube constructed in accordance with the principles of the present invention and having a sealing balloon at its distal end.
Figure 8:
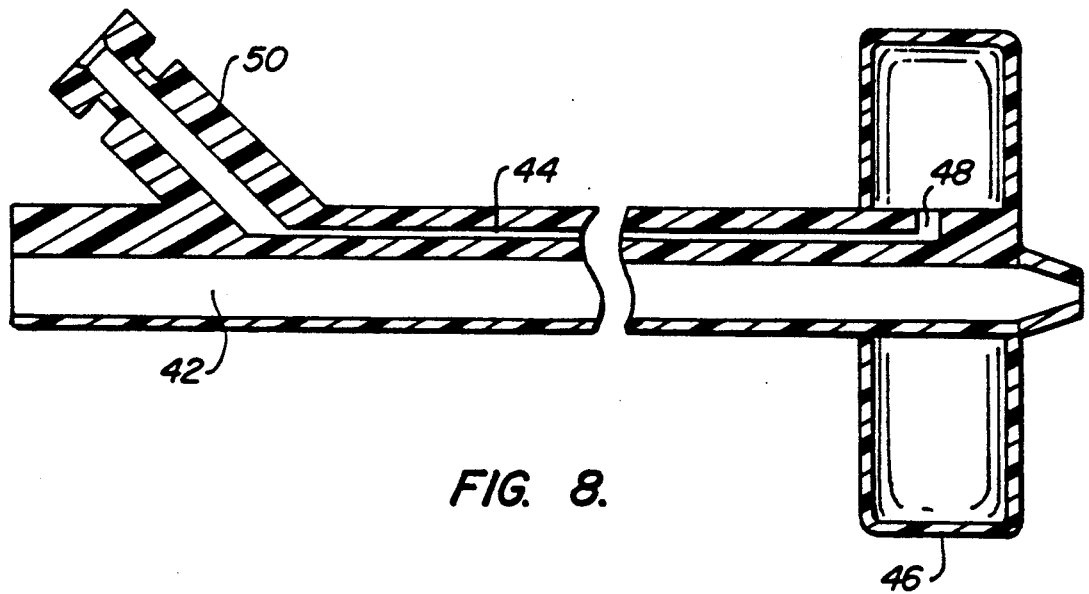
FIG. 8 illustrates the elongate dilation tube of FIG. 7, with a penetration stylet removed and the distal balloon inflated.

As shown in FIG. 7, a stylet 52 is initially present in the lumen 42, and includes a sharpened distal tip 54 which extends proximally of the dilation tube 40. After percutaneously inserting the tube 40, as described in more detail hereinbelow, the stylet 52 is removed from the lumen 42 and the balloon 46 may be inflated to effect a desired seal and retention means (FIG. 8).

Figure 9:
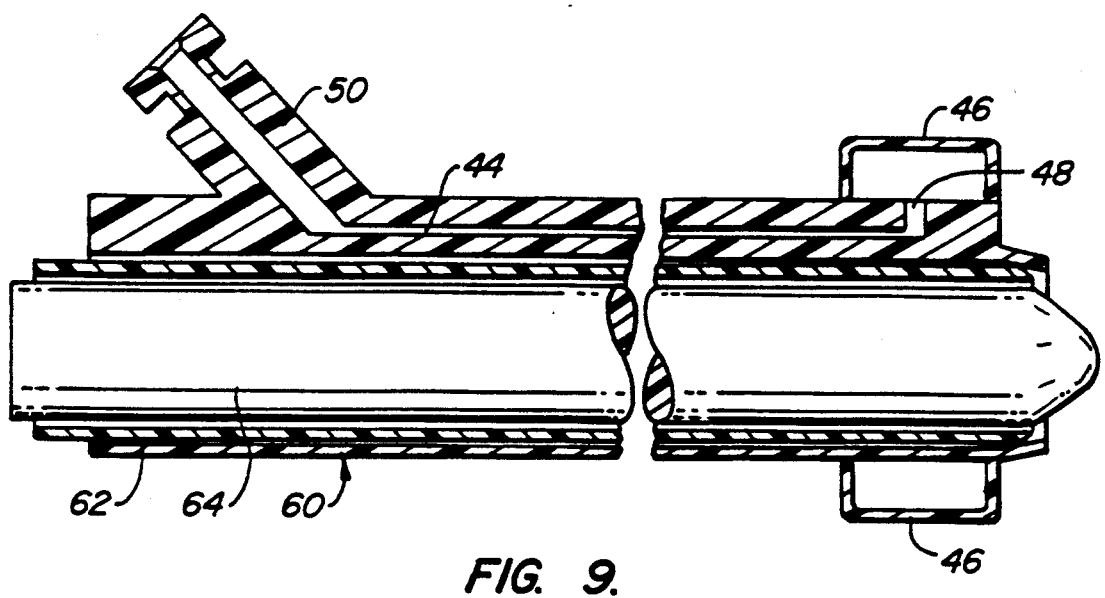
FIG. 9 illustrates the elongate dilation tube of FIGS. 7 and 8 in its radially expanded configuration with an elongate expansion member inserted in its axial lumen.
Figure 10:
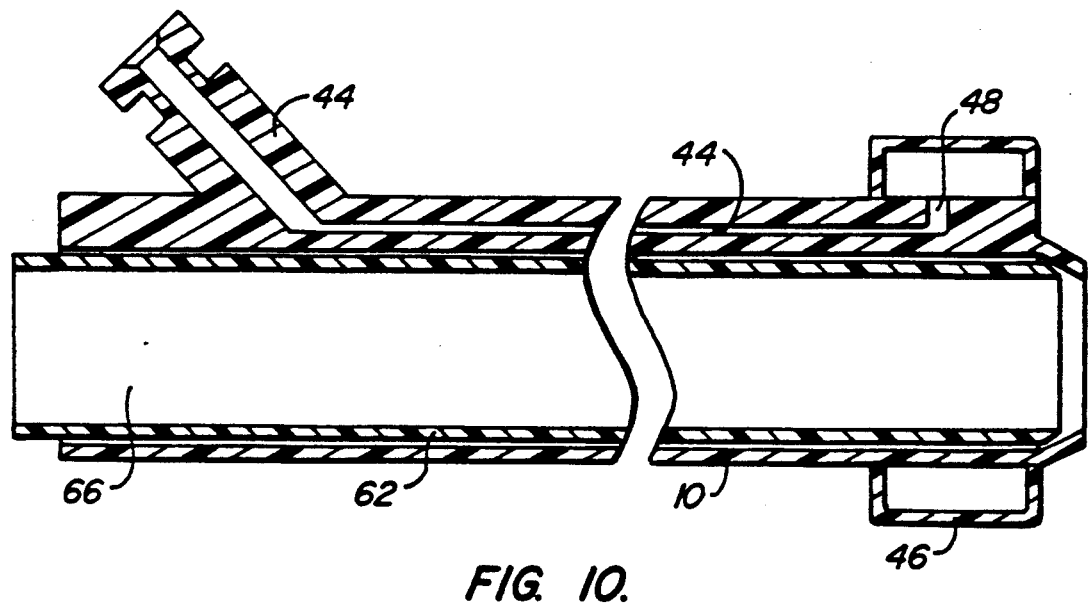
FIG. 10 illustrates the radially expanded elongate dilation tube with the inner rod of the expansion member removed to leave an enlarged access channel.

The elongate dilation tube 40 may then be expanded by axially inserting an elongate expansion member 60 including both outer tube 62 and inner rod 64, generally as described in connection with the embodiment of FIGS. 1-6. The expansion member 60 is inserted down the entire length of axial lumen 42 and results in uniform radial expansion of the dilation tube 40. It should be noted that the retention and sealing balloon 46 will be sufficiently flexible to accommodate the radial expansion of the underlying dilation tube 40. As illustrated in FIG. 9, the balloon is an integral part of the tube 40 and formed from the same material. After radial expansion of the dilation tube 40, the inner rod 64 may be removed to leave access channel 66 which is defined by the inner axial lumen of outer tube 62.

Figure 11A:
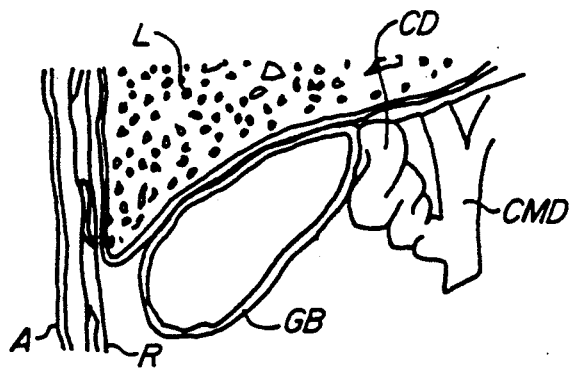
FIGS. 11A–11F illustrate a method for transperitoneal insertion and dilation of an elongate dilation tube in accordance with the method of the present invention.
Figure 11B:
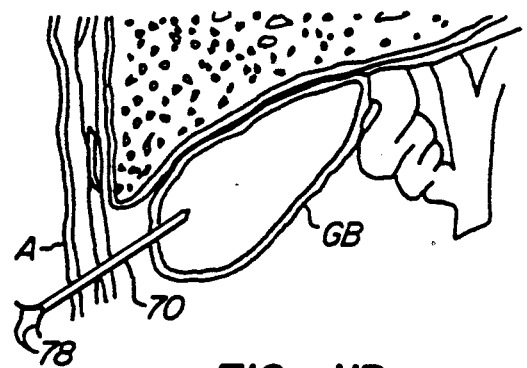
Figure 11C:
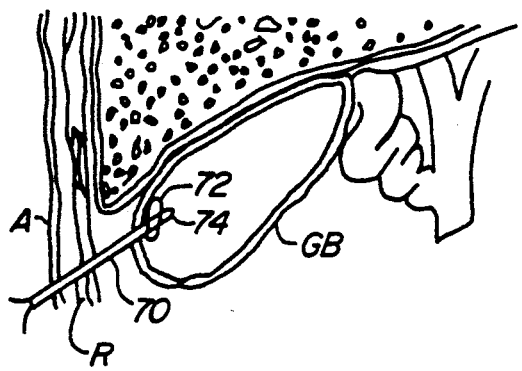

Referring now to FIGS. 11A-11F, use of the percutaneous penetration apparatus of the present invention for providing transperitoneal access to the gallbladder will be described. The gallbladder GB is located beneath the liver L and distal to the cystic duct CD and the common duct CMD (FIG. 11A). An elongate dilation tube 70 having an inflatable balloon 72 at its distal end is percutaneously introduced through the patient's abdominal wall A near the lower ribs R, as illustrated in FIG. 11B. Insertion may be effected manually and will preferably be accomplished in a single rapid thrust. Alternatively, it may be possible to employ a powered device for rapidly and accurately inserting the dilation tube 70 to the desired target location, in this case the interior of the gallbladder GB.

After insertion of the dilation tube 70 (FIG. 11C), the balloon 72 is inflated and effects a seal against the penetration through the gallbladder wall. This is a particularly advantage since it minimizes or prevents leakage of bile from the gallbladder GB into other body regions.

Figure 11D:
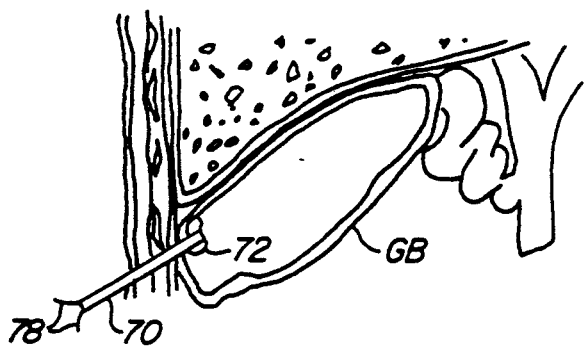
Figure 11E:
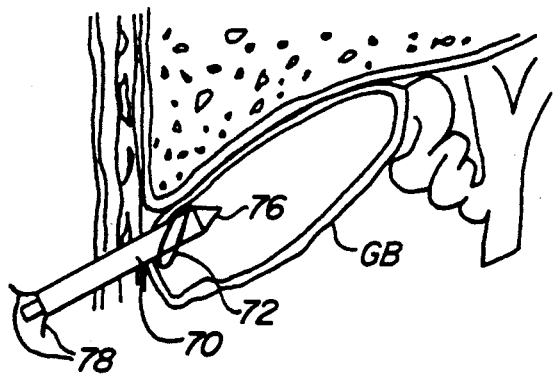
Figure 11F:
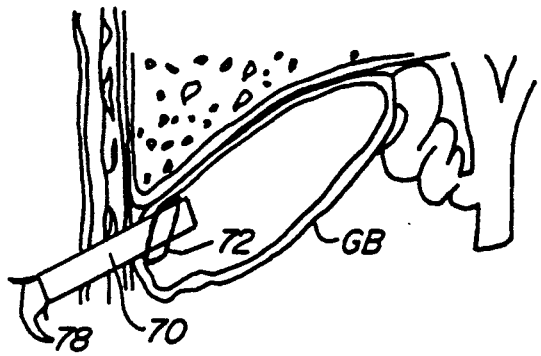

After the dilation tube 70 is inserted and the balloon 72 inflated, the stylet 74 may be withdrawn, and the tube 70 drawn outward to further effect sealing and bring the gallbladder GB into closer proximity to the surface of the skin (FIG. 11D). While the dilation tube 70 remains in such a retracted configuration, elongate expansion member 76 is inserted to provide the desired radial expansion. The user will typically hold onto proximal tabs 78 while the expansion member 76 is being inserted. In this way, axial tension is maintained on the dilation tube 70 to facilitate introducing the expansion member 76 and assure that no damaging axial force is applied to the surrounding tissue (FIG. 11E). After the expansion member 76 has been fully inserted through dilation tube 70, the expansion member or a portion thereof may be removed in order to open the desired access channel to the gallbladder GB (FIG. 11E). Thermal ablation procedures may then be performed in accordance with the methods of copending application Ser. Nos. 07/407,839; 07/529,077; and 07/551,971, the disclosures of which have previously been incorporated herein by reference.

The percutaneous penetration apparatus of the present invention may also be used for long term placement of feeding catheters, drainage catheters, drug administration catheters, and the like. Conveniently, the outer tube of the elongate expansion member may serve as the access catheter. Alternatively, the outer tube or expanded dilation member may provide the enlarged access channel for insertion of a separate catheter to achieve the desired purpose. In either case, means will be provided for fixing or retaining the exterior of the outer tube or dilation tube at the point where it penetrates the patient's skin. Retention may be achieved using conventional clips and the like which may hold the dilation tube in place with the tissue layers compressed with the expanded balloon.

Although the foregoing invention has been described in detail for purposes of clarity of understanding, it will be obvious that certain modifications may be practiced within the scope of the appended claims.

What is claimed is:

1. An apparatus for forming and enlarging a penetration, said apparatus comprising:
   an elongate dilation tube having a proximal end, a distal end, and an axial lumen, said tube being radially expandable from a small diameter to a larger diameter; and
   an elongate expansion member which is insertable through the axial lumen of the dilation tube from its proximal end to effect radial expansion of the dilation tube, said expansion member comprising an outer tube and an inner rod member, whereby the rod can be removed from the tube after expansion of the dilation tube to leave an access lumen through the inner tube.

2. An apparatus as in claim 1, wherein the elongate dilation tube comprises an elastic tubular member having a lubricous coating on its axial lumen.

3. An apparatus as in claim 1, wherein the elongate dilation tube comprises an outer sheath and a separate lubricous inner sleeve.

4. An apparatus as in claim 3, wherein the lubricous inner sleeve is nested to facilitate expansion.

5. An apparatus as in claim 1, further comprising:
   means at the distal end of the tube for puncturing tissue and organs as the tube is advanced.

6. An apparatus as in claim 5, wherein the means for puncturing comprises a stylet which is present in the lumen of the elongate dilation tube and which has a sharpened tip which extends distally of the distal end of the tube.

7. An apparatus as in claim 5, wherein the means for puncturing is a sharpened tip formed at a distal end of the elongate dilation tube.

8. An apparatus as in claim 1, wherein the rod has a tapered end which extends distally of the outer tube, whereby the tapered end facilitates insertion of the elongate expansion member into the lumen of the elongate dilation tube.

9. An apparatus as in claim 1, wherein the elongate expansion member has an outer diameter which is at least two fold larger than the diameter of the dilation tube lumen.

10. An apparatus as in claim 1, further comprising an inflatable balloon at the distal end of the elongate dilation tube and means for inflating the balloon from the proximal end of the elongate dilation tube to effect retention of the tube within and sealing of the percutaneous penetration.

11. A method for enlarging a penetration, said method comprising:
   penetrating an elongate dilation tube having an axial lumen through tissue or a duct so that a distal end thereof lies at a target location within a body;
   securing a proximal end of the elongate tube; and
   inserting an elongate expansion member comprising an outer tube and an inner rod through the axial lumen of the dilation tube from its proximal end to cause radial expansion of the tube; and
   removing the inner rod from a lumen of the outer tube, whereby the outer tube lumen provides an access channel to the target location.

12. A method as in claim 11, further comprising inflating a balloon at the distal end of the elongate dilation tube to enhance sealing of the dilation tube within the percutaneous penetration and to hold tissue layers together.

13. A method as in claim 11, wherein the target location is selected from the group consisting of solid tissue, the gallbladder, urinary bladder, kidneys, intestines, stomach, lungs, peritoneum, rectum, and uterus.

14. A method as in claim 11, wherein the elongate dilation tube has a sharpened distal tip and is penetrated without a previous puncture track.

15. A method as in claim 11, wherein the elongate dilation tube is inserted through a previously formed puncture track.

16. A method as in claim 11, wherein a stylet is present in the lumen of the elongate dilation tube and a sharpened tip of the stylet extends distally of the elongate tube to facilitate percutaneous penetration, said method further comprising removing the stylet prior to inserting the elongate expansion member.

17. A method as in claim 11, wherein the outer tube is subsequently utilized as a drainage or feeding catheter.

18. A method as in claim 11, wherein the proximal end of the dilation tube is secured manually during insertion of the elongate expansion member.

19. A method as in claim 11, wherein the proximal end of the expanded dilation tube is secured and fixed against the skin to prevent inward migration of the tube and inhibit infection of the penetration.

20. An apparatus for forming and enlarging a penetration, said apparatus comprising:
   an elongate dilation tube having a proximal end, a distal end, and an axial lumen, said tube being radially expandable from a small diameter to a larger diameter;
   an elongate expansion member which is insertable through the axial lumen of the dilation tube from its proximal end to effect radial expansion of the tube;
   an inflatable balloon at the distal end of the elongate dilation tube; and
   means for inflating the balloon from the proximal end of the elongate dilation tube to effect retention of the tube within and sealing of the penetration.

21. An apparatus as in claim 20, wherein the elongate dilation tube comprises an elastic tubular member having a lubricous coating on its axial lumen.

22. An apparatus as in claim 20, wherein the elongate dilation tube comprises an outer sheath and a separate lubricous inner sleeve.

23. An apparatus as in claim 22, wherein the lubricous inner sleeve is nested to facilitate expansion.

24. An apparatus as in claim 20, further comprising:

means at the distal end of the tube for puncturing tissue and organs as the tube is advanced.

25. An apparatus as in claim 24, wherein the means for puncturing comprises a stylet which is present in the lumen of the elongate dilation tube and which has a sharpened tip which extends distally of the distal end of the tube.

26. An apparatus as in claim 24, wherein the means for puncturing is a sharpened tip formed at a distal end of the elongate dilation tube.

27. An apparatus as in claim 20, wherein the elongate expansion member comprises a rod and outer tube assembly, wherein the rod is received in a lumen of the tube and has a tapered end which extends distally of the outer tube, whereby the assembly can be inserted into the lumen of the elongate dilation tube and the rod removed after the dilation tube has been fully expanded.

28. An apparatus as in claim 20, wherein the elongate expansion member has an outer diameter which is at least two fold larger than the diameter of the dilation tube lumen.

29. A method for enlarging a penetration, said method comprising:
penetrating an elongate dilation tube having an axial lumen through tissue or a duct so that a distal end thereof lies at a target location within a body;
securing a proximal end of the elongate dilation tube;
inflating a balloon at the distal end of the elongate dilation tube to enhance sealing of the dilation tube within the penetration and to hold tissue layers together; and
inserting an elongate expansion member through the axial lumen of the dilation tube from its proximal end to cause radial expansion of the tube, whereby an axial lumen of the expansion member provides a access channel to the target location.

30. A method as in claim 29, wherein the target location is selected from the group consisting of solid tissue, the gallbladder, urinary bladder, kidneys, intestines, stomach, lungs, peritoneum, rectum, and uterus.

31. A method as in claim 29, wherein the elongate dilation tube has a sharpened distal tip and is penetrated without a previous puncture track.

32. A method as in claim 29, wherein the elongate dilation tube is inserted through a previously formed puncture track.

33. A method as in claim 29, wherein a stylet is present in the lumen of the elongate dilation tube and a sharpened tip of the stylet extends distally of the elongate tube to facilitate penetration through tissue, said method further comprising removing the stylet prior to inserting the elongate expansion member.

34. A method as in claim 29, wherein the elongate expansion member comprises an outer tube and inner rod, said method further comprising removing the inner rod after the elongate tube has been radially expanded so that an axial lumen of the outer tube provides the enlarged access channel.

35. A method as in claim 29, wherein the outer tube is subsequently utilized as a drainage or feeding catheter.

36. A method as in claim 29, wherein the proximal end of the dilation tube is secured manually during insertion of the elongate expansion member.

37. A method as in claim 29, wherein the proximal end of the expanded dilation tube is secured and fixed against the skin to prevent inward migration of the tube and inhibit infection of the penetration.

38. A method as in claim 29, further comprising applying an axial, outward tension on the proximal end of the elongate dilation tube after the balloon has been inflated, thereby further enhancing the seal and tissue holding provided by the balloon.

39. An apparatus for forming and enlarging a penetration, said apparatus comprising:
an elongate dilation tube having a proximal end, a distal end, and an axial lumen, said tube comprising an inner sleeve and outer elastic sheath, wherein the sleeve is radially expandable and the sheath extends substantially the entire length of the sleeve so that the sleeve may be radially expanded against a radially compressive force resulting from the elastic sheath; and
an elongate expansion member which is insertable through the axial lumen of the dilation tube from its proximal end to radially outwardly deform the sleeve against the elastic sheath, whereby the inner lumen of the tube is available as an access channel.

40. An apparatus as in claim 39, wherein the inner sleeve is nested to facilitate expansion.

41. An apparatus as in claim 39, further comprising:
means at the distal end of the tube for puncturing tissue and organs as the tube is advanced.

42. An apparatus as in claim 41, wherein the means for puncturing comprises a stylet which is present in the lumen of the elongate dilation tube and which has a sharpened tip which extends distally of the distal end of the tube.

43. An apparatus as in claim 39, wherein the means for puncturing is a sharpened tip formed at a distal end of the elongate dilation tube.

44. An apparatus as in claim 39, wherein the elongate expansion member comprises a rod and outer tube assembly, wherein the rod is received in a lumen of the tube and has a tapered end which extends distally of the outer tube, whereby the assembly can be inserted into the lumen of the elongate dilation tube and the rod removed after the dilation tube has been fully expanded.

45. An apparatus as in claim 39, wherein the elongate expansion member has an outer diameter which is at least two fold larger than the diameter of the dilation tube lumen.

46. An apparatus as in claim 39, further comprising an inflatable balloon at the distal end of the elongate dilation tube and means for inflating the balloon from the proximal end of the elongate dilation tube to effect retention of the tube within and sealing of the percutaneous penetration.

47. An apparatus as in claim 39, wherein the sleeve is composed of a plastic or metal tube, whereby the tube is progressively formed as the expansion member is advanced.

48. An apparatus as in claim 47, wherein the sleeve is composed of polyethylene or Teflon ®.

49. A method for enlarging a penetration, said method comprising:
penetrating an elongate dilation tube comprising an inner sleeve and an outer elastic sheath through tissue or a duct so that said elastic contacts such tissue or duct and a distal end of the tube lies at a target location within the body;
securing a proximal end of the dilation tube;
inserting an elongate expansion member having an axial lumen through an axial lumen of the dilation tube from its proximal end to cause radial expansion of the tube, whereby the expanded elastic sheath contacts the tissue or duct and the axial lumen of the expansion member provides an access channel to the target location.

50. A method as in claim 49, wherein the target location is selected from the group consisting of solid tissue, the gallbladder, urinary bladder, kidneys, intestines, stomach, lungs, peritoneum, rectum, and uterus.

51. A method as in claim 49, wherein the elongate dilation tube has a sharpened distal tip and is penetrated without a previous puncture track.

52. A method as in claim 49, wherein the elongate dilation tube is inserted through a previously formed puncture track.

53. A method as in claim 49, wherein a stylet is present in the lumen of the elongate dilation tube and a sharpened tip of the stylet extends distally of the elongate tube to facilitate penetration through tissue, said method further comprising removing the stylet prior to inserting the elongate expansion member.

54. A method as in claim 49, wherein the elongate expansion member comprises an outer tube and inner rod, said method further comprising removing the inner rod after the elongate tube has been radially expanded so that an axial lumen of the outer tube provides the enlarged access channel.

55. A method as in claim 49, wherein the outer tube is subsequently utilized as a drainage or feeding catheter.

56. A method as in claim 49, wherein the proximal end of the dilation tube is secured manually during insertion of the elongate expansion member.

57. A method as in claim 49, wherein the proximal end of the expanded dilation tube is secured and fixed against the skin to prevent inward migration of the tube and inhibit infection of the penetration.

58. A method as in claim 49, further comprising applying an axial, outward tension on the proximal end of the elongate dilation tube after the balloon has been inflated, thereby further enhancing the seal and tissue holding provided by the balloon.

* * * * *